US007483562B2

(12) United States Patent
Ito et al.

(10) Patent No.: US 7,483,562 B2
(45) Date of Patent: Jan. 27, 2009

(54) METHOD OF DETECTING PROTRUDENT ADHERED MATTERS AND METHOD OF MAKING SPARK PLUG USING THE SAME

(75) Inventors: Masato Ito, Nagoya (JP); Shinichiro Mitsumatsu, Nagoya (JP)

(73) Assignee: NGK Spark Plug Co., Ltd., Nagoyn (JP)

( * ) Notice: Subject to any disclaimer, the term of this patent is extended or adjusted under 35 U.S.C. 154(b) by 707 days.

(21) Appl. No.: 10/523,613

(22) PCT Filed: Aug. 7, 2002

(86) PCT No.: PCT/JP02/08075

§ 371 (c)(1),
(2), (4) Date: Feb. 7, 2005

(87) PCT Pub. No.: WO2004/015831

PCT Pub. Date: Feb. 19, 2004

(65) Prior Publication Data

US 2005/0271263 A1    Dec. 8, 2005

(51) Int. Cl.
  *G06K 9/00* (2006.01)
(52) U.S. Cl. .......................................... 382/152; 445/7
(58) Field of Classification Search .................. 382/152
  See application file for complete search history.

(56) References Cited

U.S. PATENT DOCUMENTS 6,640,002 B1 * 10/2003 Kawada ...................... 382/141

| 6,672,141 | B2 | 1/2004 | Maruoka et al. |
| 7,021,980 | B2 * | 4/2006 | Hanai ............................ 445/4 |
| 7,346,983 | B2 * | 3/2008 | Oda et al. ..................... 29/882 |
| 2002/0043099 | A1 | 4/2002 | Maruoka et al. |
| 2007/0054581 | A1 * | 3/2007 | Fujita et al. .................... 445/7 |

FOREIGN PATENT DOCUMENTS

JP       01-273188 A     11/1989
JP       08-152309        6/1996

(Continued)

OTHER PUBLICATIONS

Leo B. Baldwin, On-line dimensonal gauge for glass and plastic containers, 1993, SPIE, Proceedings SPIE vol. 2064, pp. 189-195.*

*Primary Examiner*—Matthew C. Bella
*Assistant Examiner*—Sath V. Perungavoor
(74) *Attorney, Agent, or Firm*—Morgan, Lewis & Bockius LLP

(57) ABSTRACT

Protrudent matters caused by connecting metallic materials are detected with high precision and in turn offer products of high quality, and an increase of yield. The invention sets an allowable range and a non-allowable range around an outside outline (an outline of the work to be detected) of the connected work member on the basis of a shape of an outline of a reference work member (a reference outline) becoming a reference of the connected work member in order to judge presence or absence of the outline of the work to be detected in the non-allowable range, said allowable range allowing the existence of the outline of the work to be detected, and said non-allowable range not allowing the existence of the outline of the reference work.

7 Claims, 12 Drawing Sheets

FOREIGN PATENT DOCUMENTS

| | | |
|---|---|---|
| JP | 10-89923 | 4/1998 |
| JP | 10-208044 | 8/1998 |
| JP | 11-121143 | 4/1999 |
| JP | 2001-074414 | 3/2001 |
| JP | 2002-90275 A | 3/2002 |
| JP | 2002-207011 | 7/2002 |
| JP | 2002-298123 | 11/2002 |

\* cited by examiner

METHOD OF DETECTING PROTRUDENT ADHERED MATTERS AND METHOD OF MAKING SPARK PLUG USING THE SAME

This application is a national stage application of PCT/JP02/08075 filed on Aug.7, 2002.

TECHNICAL FIELD OF THE INVENTION

The present invention relates to a method of detecting protrudent matters adhered to surfaces of metallic materials when connecting them, and a method of making spark plugs using the same.

BACKGROUND OF THE INVENTION

Conventionally, while connecting metallic materials by welding, metallic pieces as so-called spatters scatter around and cause phenomena as protrudent matters adhered to surfaces of metallic materials to be connected. Since the protrudent adhered matters worsen a normal surface of the metallic material and possibly cause deterioration of a product quality, it has been demanded to establish a method of generating no protrudent adhered matters when connecting metallic materials, or a method of exactly detecting presence or absence of the protrudent adhered matters in products.

A problem to be solved by the invention is to provide a method of detecting the protrudent matters adhered to the surfaces of metallic materials when connecting them and a method of making spark plugs using the same, enabling to detect at high precision occurrence of the protrudent adhered matters caused by connecting the metallic materials, and in turn offer products of high quality, and effectively accomplish increase of yield.

DISCLOSURE OF THE INVENTION

For solving the problem as mentioned above, the invention is to offer a method of detecting protrudent matters adhered to an outside of a work member connected with a plurality of metallic materials, the method including:

a photographing process for photographing the connected work member by a photographing instrument to create a photographic image, a confirmation process of making an outside outline of the connected work member (also called as "outline of the work to be detected" hereafter) in the photographic image correspond to a range including a non-allowable range not allowing existence of the protrudent adhered matters and confirming presence or absence of existence of the outline of the work to be detected in the non-allowable range, and a judging process of judging that protrudent adhered matters exist on the outside of the connected work member when confirming, in the confirmation process, the existence of the outline of the work to be detected in the non-allowable range.

If, as mentioned above, making the outside outline of the connected work member in the photographic image correspond to the range including the non-allowable range not allowing the existence of the protrudent adhered matters, it is possible to judge whether or not the outside outline is normal on the basis of the corresponding non-allowable range (that is, the connected work member has a shape not allowed of the existence on the outside outline in the non-allowable range), and decide an index for confirming the existence of the protrudent adhered matters. The non-allowable range may be in advance decided on the basis of the outside outline (an outline of the reference work) of a reference work material to be a reference of the connected work member, whereby the non-allowable range can be made correspond to the outside external of the connected work member.

For confirming the existence of the protrudent adhered matters, the confirmation process may adopt such a method of previously deciding a range-forming line for forming a range including the non-allowable range, moving the decided range-forming line to X-axis or Y-axis in order to make correspond to the outline of the work to be detected, and confirming whether or not the outline of the work to be detected exists in the non-allowable range. Specifically, the confirmation process may employ such a method of, on the basis of the outline of the reference work, previously setting a detecting line as a boundary between the non-allowable range and an allowable range for allowing the existence of the outline of the reference work neighboring the non-allowable range, making the correspondence between the detecting line and the outline of the work to be detected in the photographic image, and confirming whether or not the outline of the work to be detected exists on the detecting line. The correspondence between the outline of the work to be detected and the non-allowable range as well as the correspondence between the outline of the work to be detected and the detecting line may be provided in the photographic image of the connected work member, so that the correspondence can be rapidly realized with good precision. If judging the existence of the protrudent adhered matters by the method of confirming presence or absence of the outline of the work to be detected within the non-allowable range (on the detecting line), master data in advance prepared for passing the judgment is enough with only data for prescribing the non-allowable range (the detecting line), and in regard to reading out or referring to the data, the amount of dealing data is reduced, and rapid processing may be effected.

Further, in a plurality of metallic materials connected as the connected work member, reference points per members are respectively decided per members, and on the basis of the reference point per member, the detecting line may be positioned per respective metallic materials. If providing the reference point per member and exerting the method of deciding the respective detecting lines based on the reference point per member, the positional relation between the detected lines and the metallic materials can be set correctly each of the members. For example, even if a dimension in a direction almost crossing with the welded part is changed owing to connected conditions so that the positional relation between the metallic materials is more or less changes (for example, even if a thickness dimension in the welded part is a little dispersed by the welded condition), since the detecting line is set in reference to each of the members connected over across the welded part, the detecting lines are made correspond to the respective members, and set with high precision. It is thereby possible to heighten the detecting precision of the protrudent matters adhered to the outside of the connected work member.

The plurality of metallic materials include two metallic materials of different diameters, and in regard to at least one of these two metallic materials, a position changing the diameter in the outline of the work to be detected can be determined as the reference point per member. If determining the changing position in the diameter as the reference point per member, though not carrying out any complicated treatment in an obtained photographic image, since it is sufficient to only detect the changing position of a characterized diameter, the reference point per member can be easily determined. By easily determining the reference point per member, the detecting line is easily set, and the outline of the work to be detected and the detecting line can be made correspond rapidly with high precision. By the way, practically, of the outlines of the work to be detected of the connected work members of the two metallic materials of the different diameters, a peak of a square protrusion of the metallic material of the larger diameter is rendered to be a changing position of the diameter, and a distal point of the peak can be employed as the reference point per member, whereby the reference point per member can be exactly positioned in the obtained photographic image, so that the detecting line can be created with good precision, and in turn the detecting precision of the protrudent matters adhered on the outside of the connected work member can be more heightened.

Figure 1A:
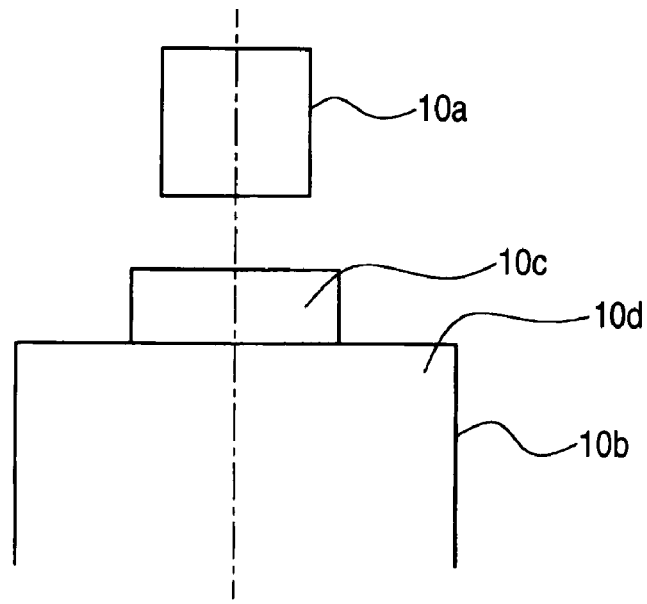
FIGS. 1A, 1B is explanatory views schematically explaining occurrence of the protrudent adhered matters in connection of the metallic material.

In the drawings, reference numeral 1 is an inspection apparatus, 10 is the connected work member, 12 is a photographing camera (the photographing instrument), $L_1$ is an outline of the reference work, $L_2$ is an outline of the work to be detected, 102, 102' are detecting lines, S is the protrudent adhered matter, $S_{10}$ is a photographing center line of the reference work member, and $S_{20}$ is the photographing center line of the connected work member.

MOST PREFERRED EMBODIMENT FOR PRACTISING THE INVENTION

Explanation will be made to an example of the invention referring to the attached drawings.

Figure 1B:
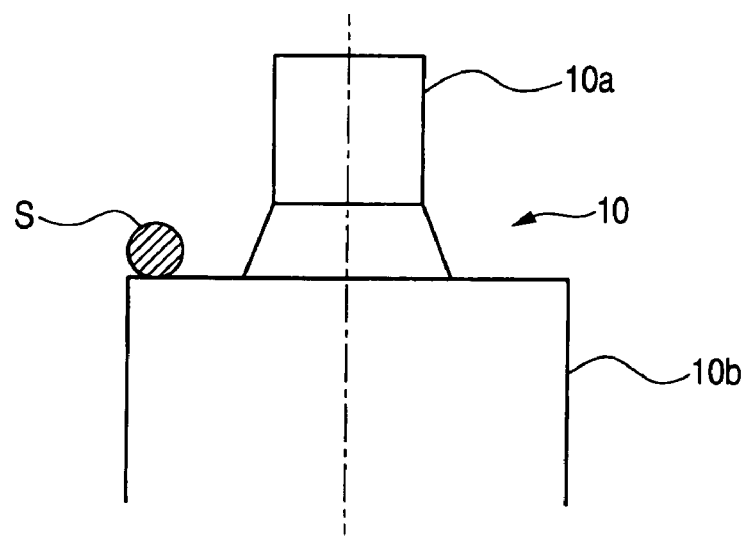

To state a summary of the invention, the method of detecting the protrudent adhered matters comprises the photographic process and the confirmation process, and in the photographic process, a plurality of metallic materials are connected to build the connected work member, and the connected work member is taken a photograph as an object for detecting adhered matters thereon via a photographing instrument, while in the confirmation process, on the photographic image of the connected work member made by the photographic process, it is confirmed whether protrudent adhered matters exist on the outside of the connected work member. FIGS. 1A-1B are the schematic views of connection of the metallic materials, and in this example, the two metallic material 10a, 10b are welded (for example, a laser welding, a resistance welding or electronic beam welding) to form the connected work member 10. The method according to the invention detects whether the protrudent adhered matters (so-called spatters) S appear on the surface of the connected work member 10.

In the example, the respective metallic materials are formed with circular columns in at least one parts thereof, and the connected work member so arranged that these circular columns are coaxial, is taken as the object for detecting the protrudent adhered matters. In an example of FIG. 1A, prior to connection, a first metallic material 10a is shaped in the circular column, and a second metallic material 10b is formed in that the two circular columns of different diameters are stepwise continuous in an axial direction. The circular column of the smaller diameter is a connecting part 10c and the circular column of the larger diameter is a seat part 10d. An end face of the connecting part 10c and an end face of the first metallic material 10a are respectively connecting faces, and are connected each other to form the connected work member 10 as shown in FIG. 1B.

Figure 6:
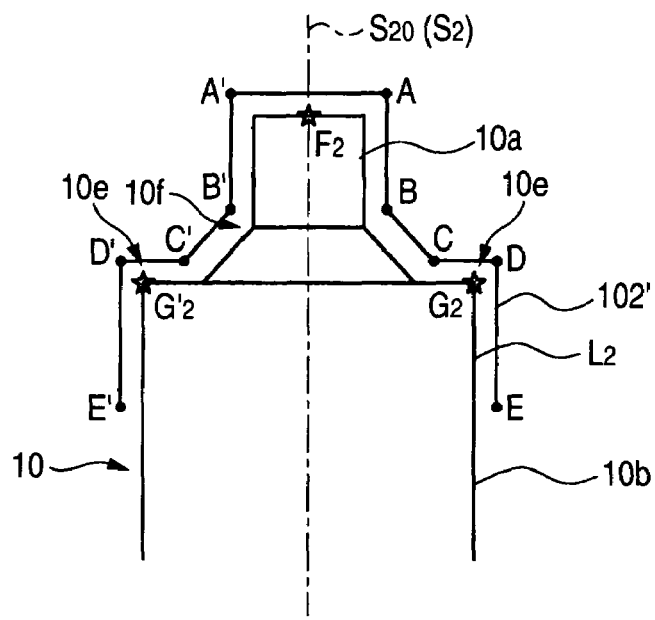
FIG. 6 is an explanatory view for explaining determination of the detecting line in the photographic image of the connected work member.

Further, as a detecting treatment of the protrudent adhered matters, there are a non-allowable range and an allowable range, and the non-allowable range is determined in a periphery of an outside outline $L_1$ (called as also "outline $L_1$ of the reference work" hereafter) of a later mentioned reference work member 100 (see FIG. 2) which is a reference of a previously determined and connected work member 10, and does not allow existence of the outline $L_1$ of the reference work (in other words, does not allow the existence of the protrudent adhered matters as spatters), while the allowable range allows the existence of the outline $L_1$ of the reference work, and the non-allowable range and the allowable range are made correspondent on the basis of the reference point determined on an outline of the work to be detected $L_2$ in a periphery of the outside outline $L_2$ (also called as "outline $L_2$ of the work to be detected" hereafter) of the connected work member 10 in the photographic image as seen in FIG. 6. The outline $L_2$ of the work to be detected is confirmed as to presence or absence in the non-allowable range. As shown in detail in FIG. 6, a detecting line 102' as a boundary between the non-allowable range and the allowable range is determined on the basis of the reference point determined on the outline $L_2$ of the work to be detected for confirming whether or not the outline $L_2$ of the work to be detected exists on the detecting line 102'. In the following description, explanation will be specifically made to this determining method and the detecting method of the protrudent adhered matters based thereon.

Figure 2:
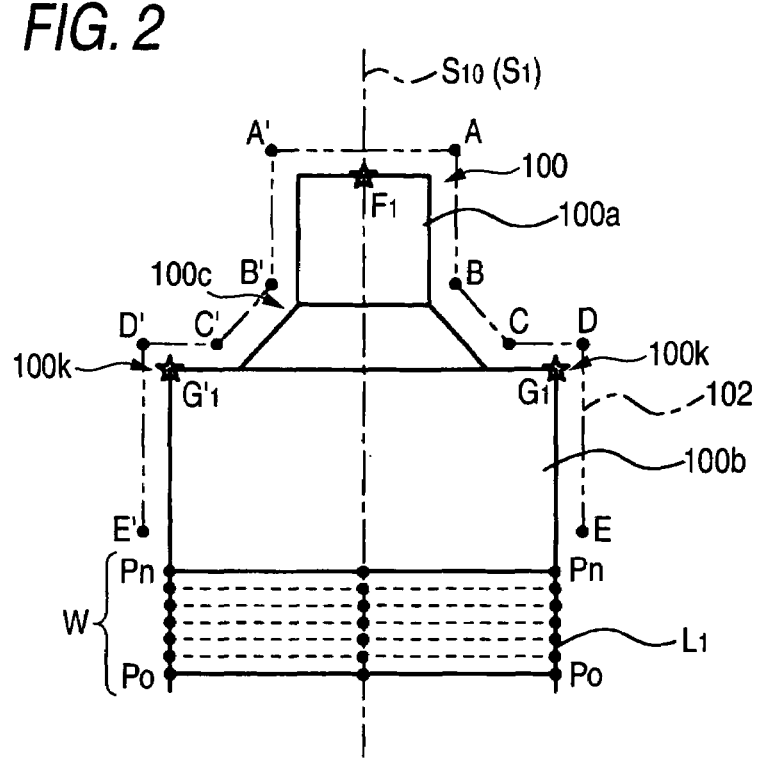
FIG. 2 is an explanatory view for explaining the reference point and the ordering point of the detecting line based on the image of the reference work member.

For setting the non-allowable range and the allowable range, at first as in FIG. 2, the detecting line 102 as a boundary between the non-allowable range and the allowable range is in advance registered as to configuration following the outline $L_1$ of the reference work. For generating the detecting line 102' corresponding to the outline $L_2$ of the work to be detected so as to reflect the positional relation between the detecting line 102 and the outline $L_1$ of the reference work, the detecting line 102 based on the reference work member 100 and the outline $L_2$ of the work to be detected are made correspondent in the photographic image taking a photograph of the connected work member as FIG. 6 (the detecting line 102 made correspondent in the photographic image is the detecting line 102'), and in the photographic image made correspondent it is confirmed whether or not the outline $L_2$ of the work to be detected exist on the detecting line 102'.

The detecting line 102 based on the reference work member 100 is positioned as follows. At first, as shown in FIG. 2, the reference work member 100 is previously photographed as one having a normal shape (no existence of the protrudent adhered matters) being the reference of the connected work member 10 by the photographing instrument (practically, photographed in the same manner as photographing the connected work member as later mentioned). Reference points (reference points per members) are set per respective members in the photographed reference work member 100. Referring to the example of FIG. 2, the reference point $F_1$ of the first member is fixed as the reference point per member in a first reference member 100a, and detecting line-ordering points A, B as well as A', B' are respectively determined in correspondence to the reference points $F_1$ of the first member.

The reference points $G_1$, $G_1'$ of the second members are fixed as the reference points per members in the second reference member 100b, and detecting line-ordering points C, D, E are set in correspondence to a reference point $G_1$ of the second member, and detecting line-ordering points C', D', E' are set in correspondence to the reference point $G_1'$ of the second member, respectively. The thus set detecting line-ordering points are made correspondent to reference points $F_2$, $G_2$, $G_2'$ set by reflecting the positions of the reference points $F_1$, $G_1$, $G_1'$ in the photographic image of the connected work member 10 as shown in FIG. 6, and are the reference positions for setting the detecting line 102' (see FIG. 6) along the outside outline $L_2$ of the connected work member 10.

Figure 13:
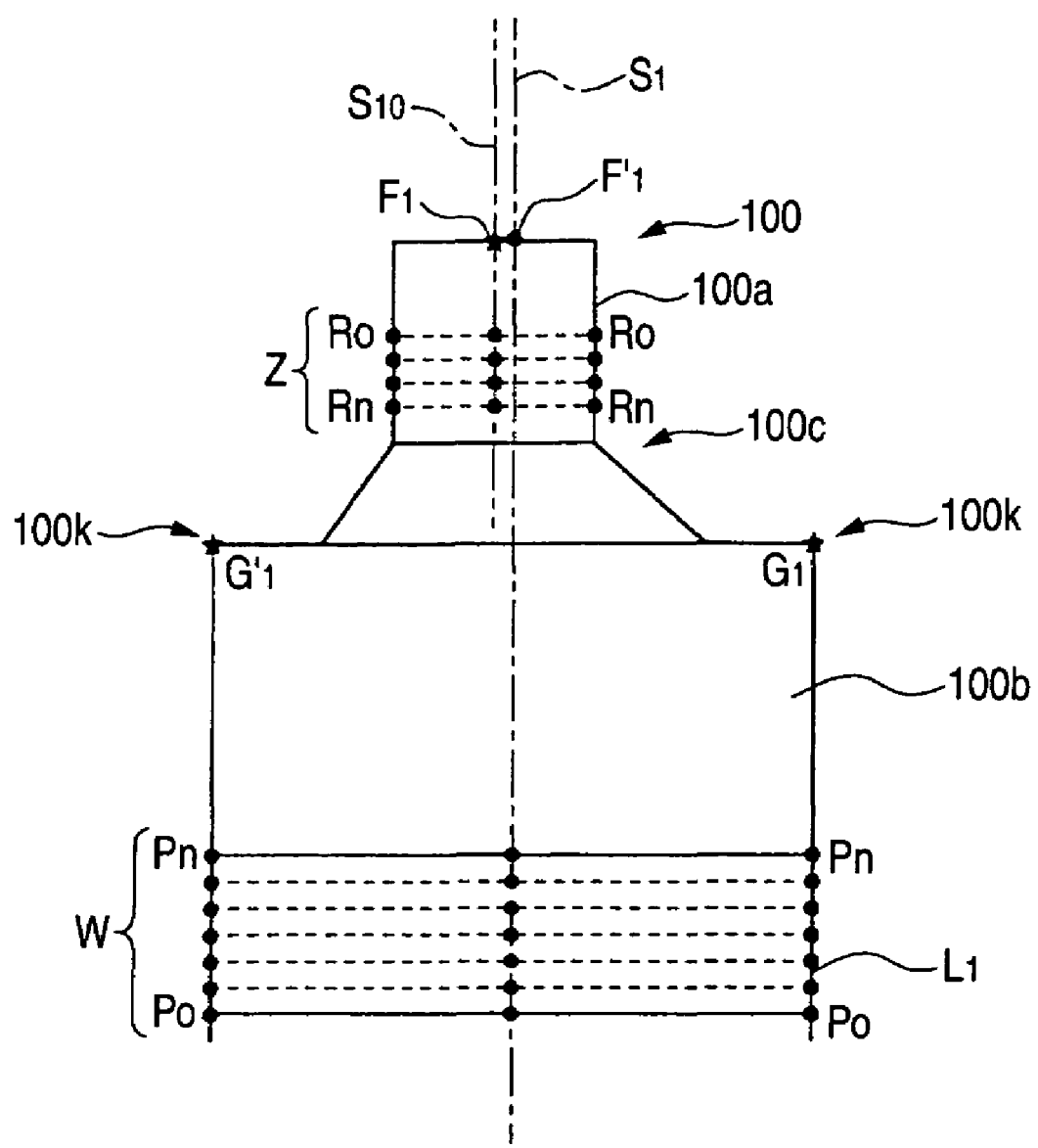
FIG. 13 is an explanatory view showing a method of determining the reference points of the first member.

The reference point is determined in the reference work member 100 as follows. At first, based on the image of the photographed reference work member 100, a temporary central axial line $S_1$ of the reference work member 100 in the photographic image (also called briefly as "central axial line $S_1$" hereafter, corresponding to a later mentioned temporary image central axial line $S_1$) is determined. Specifically, as shown in FIG. 2, in plural positions of prescribed intervals (in FIG. 2, intervals W) of the second metallic material 100b of the reference work member 100, measuring lines (measuring lines $P_0$-$P_0$ . . . Pn-Pn) are determined, and regarding directions of the measuring lines as width directions, measurement is made to a width of the second metallic material 100b. Practically, the measuring lines in prescribed coordinate direction in the photographic image are drawn in parallel at fixed intervals. Besides, crossing points (crossing points $P_0$-$P_0$ . . . crossing points Pn-Pn) between the measuring lines and the outline $L_1$ of the reference work are fixed, and regarding the crossing points as widths, centers of the widths are determined as central points. Further, as shown in FIG. 13, a straight formula for prescribing the temporary central axial line $S_1$ based on the plural central points to be determined, is demanded by a regression formula based on these plural central points (for example, the straight formula based on a method of least square). The decided straight formula is made a temporary central axial line $S_1$, and at the same time, crossing points with the outline $L_1$ of the reference work in the temporary central axial line $S_1$ are temporary reference points $F_1'$ of the first member. Practically, the crossing point with the outline $L_1$ of the reference work in the side of the first metallic material 100a is the temporary reference point $F_1'$ of the first member.

By the way, the above mentioned temporary reference point $F_1'$ of the first member may be, as it is, utilized as a regular reference point and the temporary image central axial line $S_1$ may be utilized as a regular image central axial line, but if determining the regular reference point and the regular image central axial line as follows, determining precision can be more heightened. As shown in FIG. 13, in plural positions of fixed intervals Z shifted to a lower side of FIG. 13 (toward the second member) by a size previously determined from the temporary first reference point of the member $F_1'$ determined as mentioned above, a plurality of measuring lines of the first metallic material 100a are determined in parallel in the prescribed coordinate direction. Crossing points (crossing point $R_0$, $R_0$ . . . crossing points Rn, Rn) between the measuring lines and the outline $L_1$ of the reference work are set, and regarding as widths the intervals between central points being the crossing points, centers of the widths are determined. Further, the straight formula for prescribing the temporary central axial line $S_{10}$ (corresponding to a later mentioned image central axial line $S_{10}$) based on the plural central points to be determined, is demanded by the regression formula based on these plural central points (for example, the straight formula based on the method of least square). The central axial line $S_{10}$ for the first metallic material 100a in the photographed image is decided as FIG. 13, and a crossing point between the central axial line $S_{10}$ and the outline $L_1$ of the reference work is finally set as the reference points $F_1$ of the first member. Thus, if providing the central axial line $S_{10}$ of the first metallic material 100a and setting the reference points $F_1$ of the first member, even if the first metallic material 100a is more or less offset with respect to the central axial line $S_1$ owing to a welding, the reference point per member is settled to the first metallic material 100a at good precise, so that the precision of setting the detecting line and detecting spatters may be heightened. By the way, although FIG. 13 omits the detecting line in the explanation, it is set on the basis of the reference points $F_1$, $G_1$, $G_1'$ by the same technique as in FIG. 2. FIG. 2 shows the example that the central axial line $S_{10}$ agrees with the temporary central axial line $S_1$.

Figure 11:
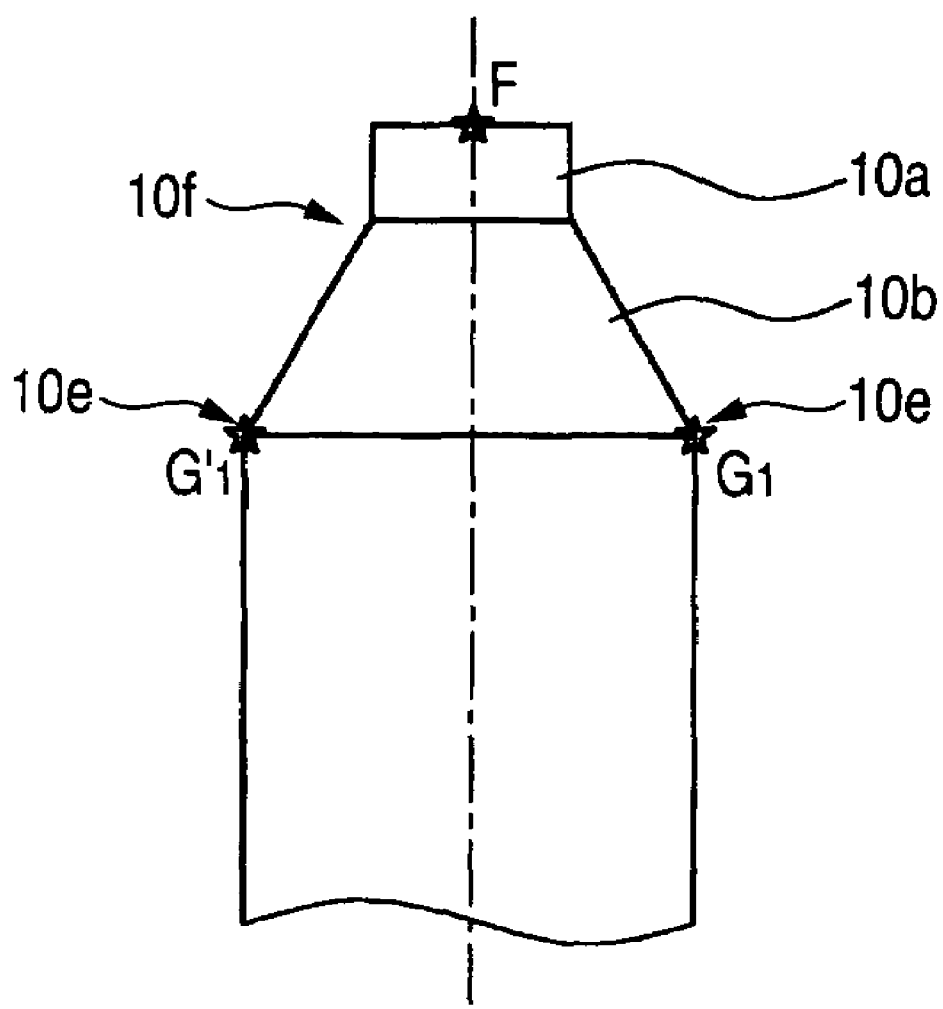
FIG. 11 is a view showing another example of the connected work member.

In the side of the second metallic material 100b, changing positions of the widths in the outline $L_1$ of the reference work are set as the reference points $G_1$, $G_1'$ per members. In the example of FIG. 2, a point that the outline $L_1$ of the reference work is discontinuous, is the changing position of the width, and projections 100k, 100k are formed with the discontinuous points being peaks. The peaks of the projections 100k, 100k are reference points per members (the second reference points of the members G1, G1'). In the example of FIG. 2, the projections are formed to be rectangular, but not limiting thereto, for example, as seen in FIG. 11, such a connected work member 10 may be aimed at, which (member 10) is formed with projections 10e having the outline of the reference work being obtuse angle. Otherwise, the projection may be substantially square. For example, the reference point per member may be settled continuously to the projection 10e having the outline of the reference work $L_1$ projecting in curve.

Figure 12A:
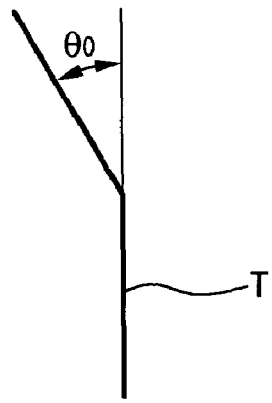
FIGS. 12A-12D are views showing examples of detecting methods of the reference points.
Figure 12B:
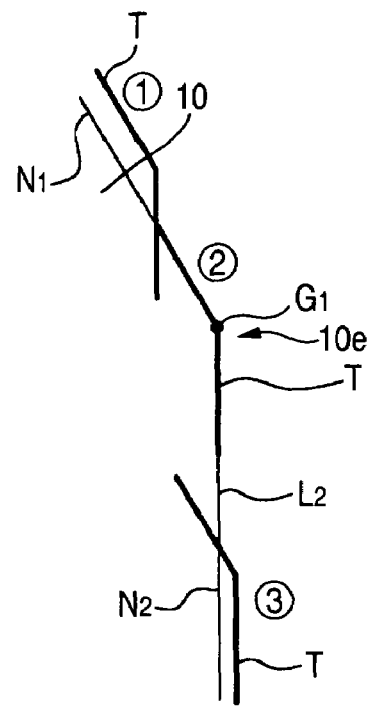
Figure 12C:
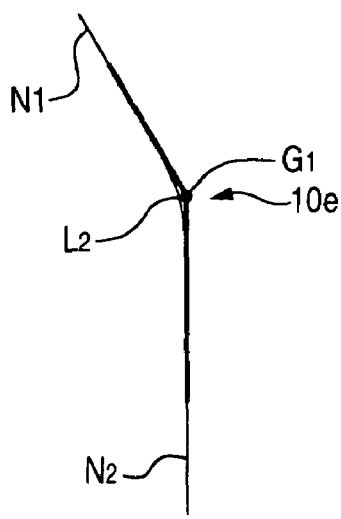
Figure 12D:
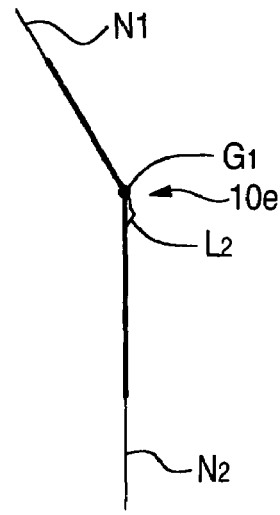

A determining method of the reference point per member at the projection, as shown in FIGS. 12A-12D, may determine the crossing point as the reference point per member (the reference point $G_1$ of the second member), which (crossing point) is kept between both sides of the straight line parts $N_1$, $N_2$ of the projection 10e of the outline $L_2$ of the work to be detected (the same even in the outline $L_1$ of the reference work) or which is on extensions of the straight line parts $N_1$, $N_2$. Specifically, at first, as FIG. 12A, a template T shaped in square is prepared which is a reference of the projection 10e. Further, as FIG. 12B, a position is sought for which is most matched to the shape of the template T in the outline $L_2$ of the work to be detected. In FIG. 12B, a position 2 is matched, and the peak of the template T at the matched position is set as a peak of the projection (that is, a reference point per member (the reference point $G_1$ of the secondary member)). As seen in FIG. 12C, even if the projection 10e is curved in the outline $L_2$ of the work to be detected, or as FIG. 12D, even if the projection is not under a good surface condition (for example, even if such as a bur exists nearly the projection 10e), it is possible to set the reference point per member (the reference point $G_1$ of the secondary member).

Further, as FIG. 2, in case the reference work member 100 projects to an imaginary plan in parallel to its own central axial line (omitting a drawing: "its own central axial line" referred to herein is meant by the central axial line of the reference work member 100 itself, and distinguishes from the central axial line on the projected image), the reference work member 100 uses a linearly symmetrical central axial line as a symmetrical axis of the central axial line $S_{10}$ on the projected image (also called as "image central axial line $S_{10}$" hereafter). Reasonably, as FIG. 6, the connected work member 10 also have the symmetrical shapes. In the reference work member 100 as shown in FIG. 2, in case one side as to the image central axial line $S_{10}$ in the outline $L_1$ of the reference work is rendered to be a first side and another side is to be a second side, mutually symmetrical reference points are respectively settled at the first side and at the second side (in FIG. 2, a right side is the first side and the opposite side is the second side). Based on the reference point in the first side (the first side reference point), an ordering point for prescribing a detecting line position of the first side (also called as "the ordering point of the first side-detecting line" hereafter) is decided, and similarly, based on the reference point in the second side (the reference point of the second side) is decided.

Figure 3:
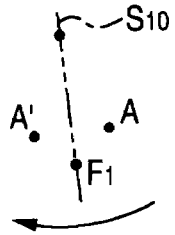
FIG. 3 is an explanatory view for explaining determination of an ordering point of a second side-detecting line based on an ordering point of a first side-detecting line.
Figure 4:
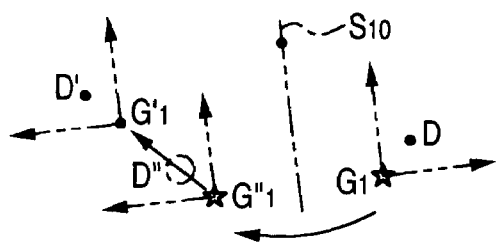
FIG. 4 is a view showing another example of FIG. 3.

Practically, the positional relation between the second side reference point and the ordering point of the second side detecting line is symmetrical concerning the image central axial line $S_{10}$ with respect to the positional relation between the first side reference point and the ordering point of the first side-detecting line, and in such a way, the ordering point of the second side detecting line can be automatically settled on the basis of positional information of the first side reference point, the second side reference point and the ordering point of the first side detecting line. "Automatically settled" referred to herein is meant by not manual input but treatment of automatically generating the ordering point of the second side detecting-line based on the information of the respective points. FIGS. 3 and 4 show practically technical examples as to the automatic settlement.

FIG. 3 shows an example of deciding an ordering point A' of the detecting line based on the decided ordering point A of the detecting line and the symmetrical axis $S_{10}$ (that is, the above mentioned image central axial line $S_{10}$), while FIG. 4 shows an example of deciding an ordering point D' of the detecting line based on the ordering point D of the detecting line and the symmetrical axis $S_{10}$. FIG. 3 decides the ordering point A' of the detecting line at the symmetrical position concerned with the symmetrical axis (the image central axial line $S_{10}$) of the ordering point A of the detecting line. That is, in case the reference point is positioned, like the reference point $F_1$, on the symmetrical line, it functions as both reference points of the first side reference point and the second side reference point. In FIG. 4, in regard to the symmetrical axis (the image central axial line $S_{10}$) of the ordering point D of the detecting line and the reference point $G_1$ (the first side reference point) of the second member a symmetrical position $G_1''$ (parts of broken lines) is determined, and based on the positional relation of the symmetrical position. $G_1''$ and the reference point $G_1'$ of the second member (the second side reference point), the symmetrical position D'' of the ordering point D of the detecting line is corrected to determine the ordering point D' of the detecting line. Depending on this practice, even if an error is caused in the symmetrical relation as to the symmetrical axis $S_{10}$ of the reference point $G_1$ of the second member (the first side reference point) and the reference point $G_1'$ of the second member (the second side reference point), the ordering point D' of the detecting line can be automatically determined exactly on the basis of the position of the reference point $G_1'$ of the second member. If employing the above method, the ordering points A' to E' of the detecting lines can be automatically determined on the basis of the ordering points A to E of the detecting lines, and effort for determining the ordering points of the detecting lines can be much reduced.

In the above explanation, the symmetrical axis is the image central axial line $S_{10}$, but in the first metallic material 100a and the second metallic material 100b, individual symmetrical axes may be determined respectively in order to determine the reference points as mentioned above. That is, in the first reference member 100a, the image central axial line $S_{10}$ is decide as the symmetrical axis, and in the second reference member 100b, the temporary image central axial line $S_1$ is decided as the symmetrical axis.

A memory is in advance stored with data (relative positional data) for prescribing the relative positions of the ordering points A to E and A' to E' of the respective detecting lines to the outline $L_1$ of the reference work. The relative positional data may specifically store relative coordinate data determining the coordinate relation between the reference point per member of the reference work member 100 and the ordering points of the respective detecting lines. For example, the relative coordinate data of the ordering point A of the detecting line corresponding to the first reference points of the member $F_1$ may respectively store X coordinate values and Y coordinate values of the ordering point A of the detecting line on an origin of the reference point $F_1$ of the first member in case the image plan is X-Y plan. In such a manner, if the reference point $F_2$ is decided in correspondence to the reference point $F_1$ of the first member in the work member 10 to be detected, the ordering point A of the detecting line can be decided as the origin of the reference point $F_2$ by the relative coordinate data. The same practice may be applied to a case of deciding the relative positional data of the ordering points C, D, E of the detecting lines in correspondence to the reference point $G_1$ of the second member, and also to a case of deciding the relative positional data of the ordering points C', D', E' of the detecting lines in correspondence to the reference point $G_1$'s of the second member.

Figure 10:
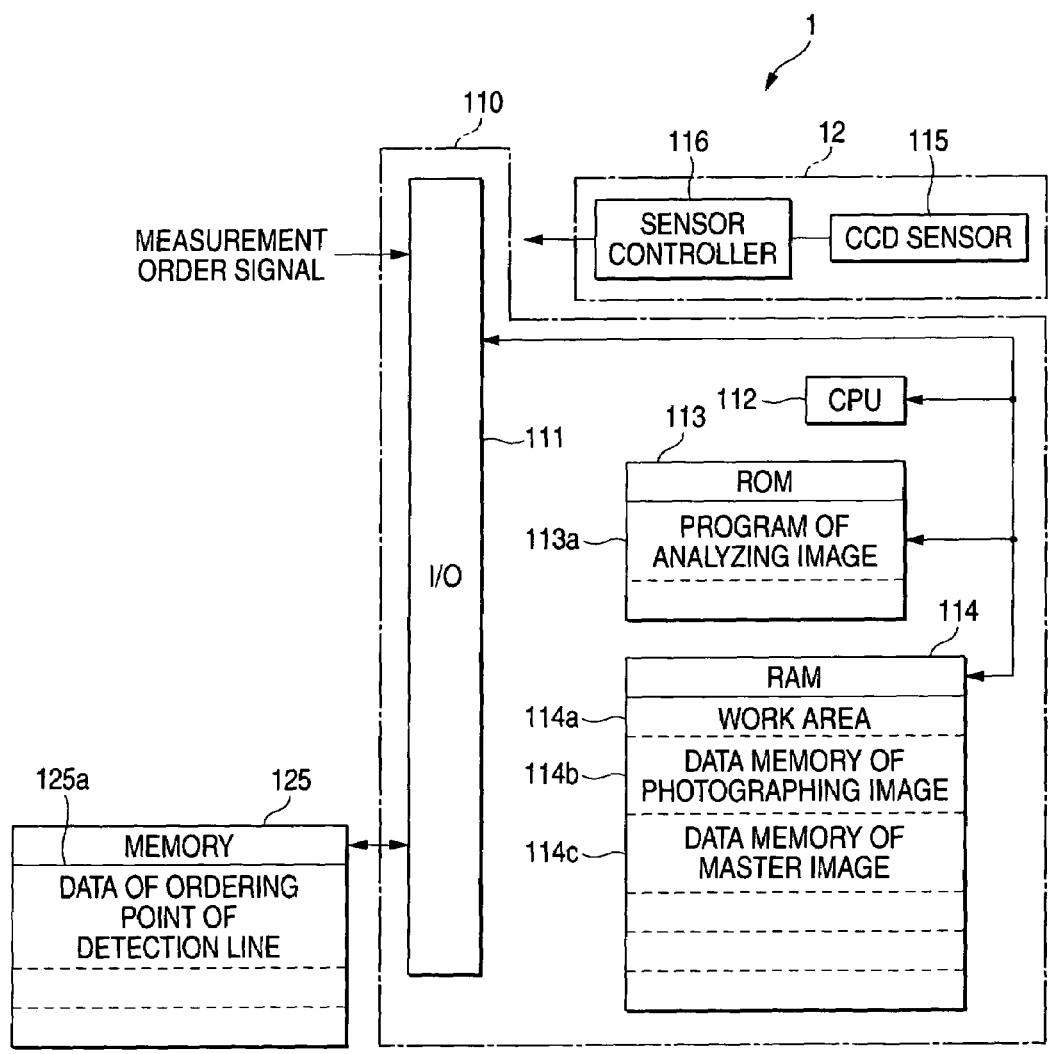
FIG. 10 is a block diagram showing one example of an electrical structure of the detecting apparatus of FIG. 7.

The data of the ordering points A to E and A' to E' of the respective detecting lines prescribed on the reference points (the reference point $F_1$ of the first member, and the reference points $G_1$, $G_1'$ of the second members) are stored as the ordering data 125a of the detecting line in the memory 125 of FIG. 10 such that the data are enabled to be read out in the confirmation process. By using the ordering data 125a of the detecting line in the memory 125, if, for example, the reference point $F_2$ corresponding to the reference point $F_1$ in the outline $L_1$ of the reference work is determined in the outline $L_2$ of the work to be detected, the ordering points A, A' and B, B' can be determined in correspondence to the reference point $F_2$, and similarly, if the reference points $G_2$, $G_2$' corresponding to the reference points $G_1$, $G_1$' are ascertained, the ordering points C, C', D, D', E, E' of the detecting lines are fixed on the obtained images correspondingly.

Next, explanation will be made to a specific flow of the detecting method of the protrudent adhered matters.

At first, a structure of an apparatus will be stated, referring to FIG. 10. FIG. 10 shows a block diagram concerning an example of an electrical structure of an inspection apparatus 1 (see FIG. 7) used to the detecting method of the invention. The inspection apparatus 1 comprises a photographic camera 12 functioning as a photographic instrument supported on a frame (not shown) and an analyzing part 110 connected thereto. The analyzing part 110 is composed of I/O port 111 and CPU 112, ROM 113 and RAM 114 connected thereto. CPU 112 functions as an instrument exerting a treatment (FIG. 5) following a later mentioned flow chart on the basis of an image analyzing program 113a stored in ROM 113. The photographic camera 12 is composed as CCD camera having an image detecting part of, e.g., a two dimensional CCD sensor 115 and having a sensor controller 116, and as FIG. 7, to decide a transverse direction to the central axial line $S_2$' of the connected work member 10 as a photographing direction.

Figure 5:
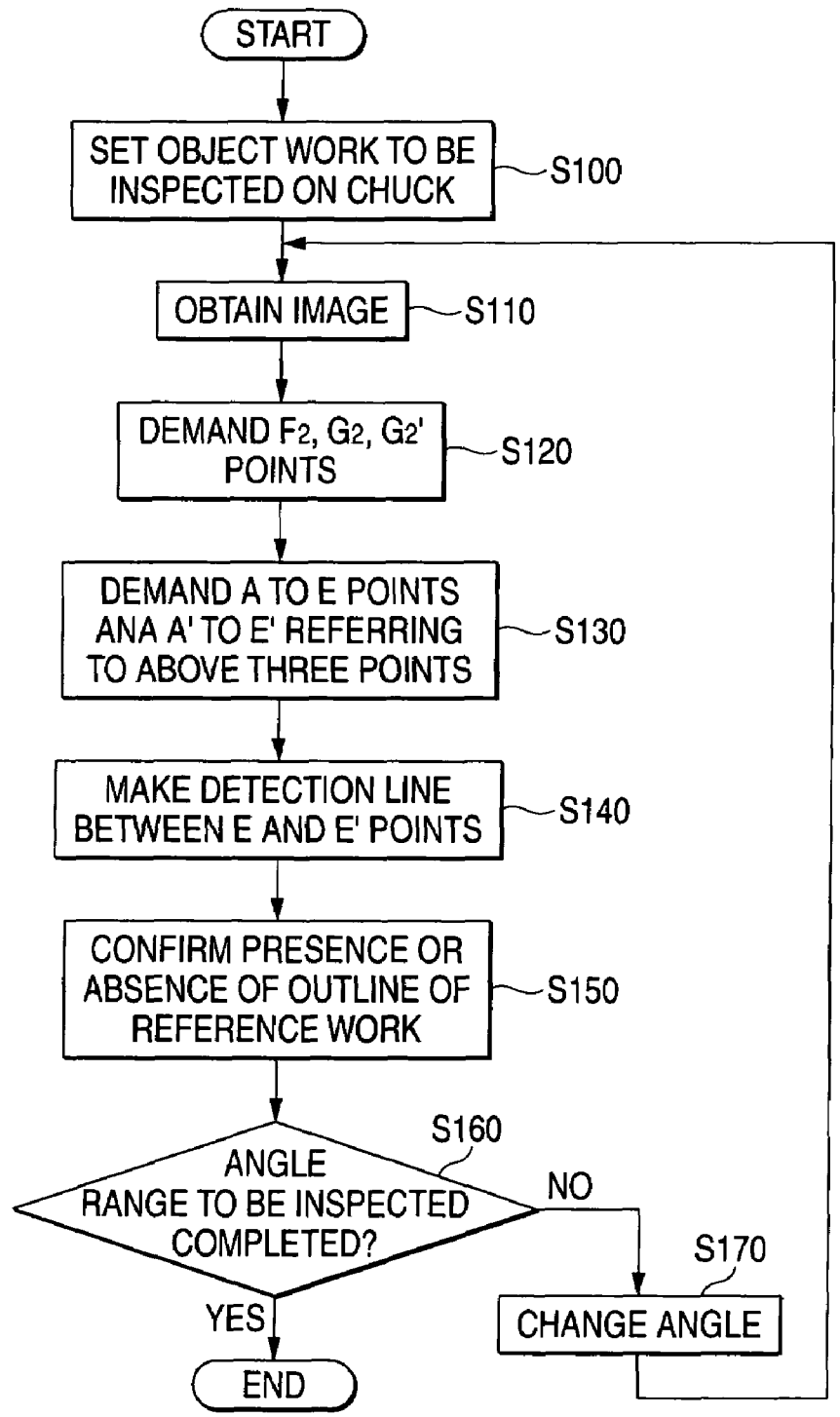
FIG. 5 is a flow chart showing one example of a specific flow of a method of detecting the protrudent adhered matters according to the invention.
Figure 7:
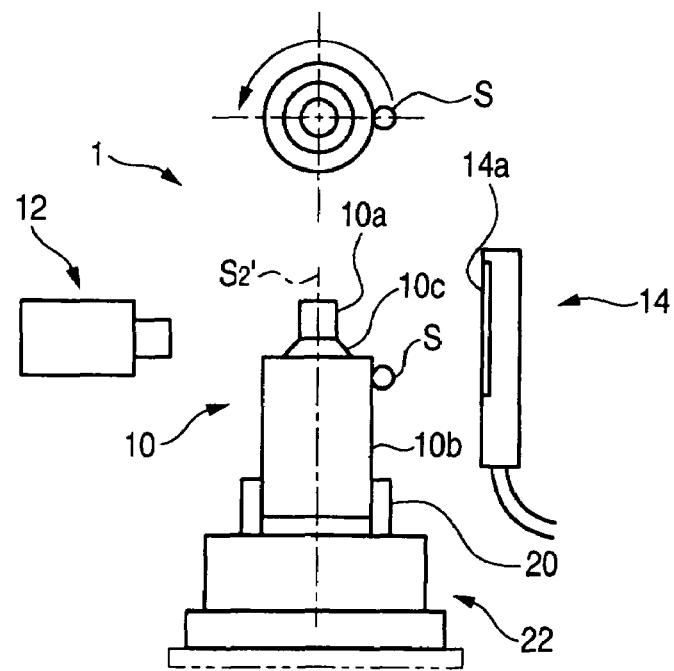
FIG. 7 is a view schematically showing a detecting apparatus.
Figure 8:
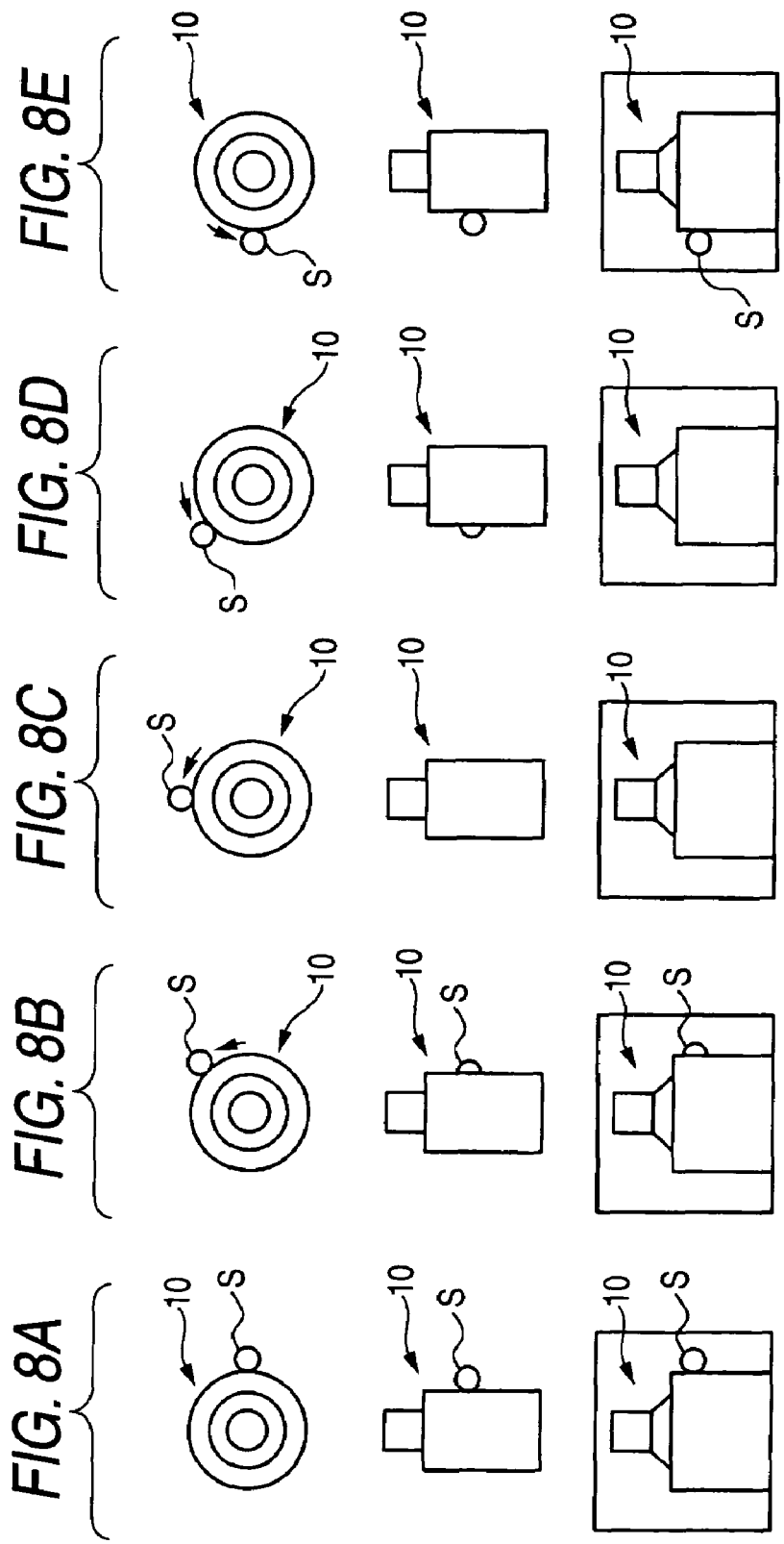
FIGS. 8A-8E are explanatory views for schematically explaining photographs at various angular positions.

FIG. 5 shows the flowchart of one example of the detecting treatment, and this detecting treatment is exerted mainly by CPU 112 based on the image analyzing program 113a shown in FIG. 10. Firstly, when the detecting treatment is started, the connected work member 10 is secured (S100) by a chuck part 20 in a work holding part 22 of the inspection apparatus 1 as shown in FIG. 7. The work holding part 22 is rotatable around a rotation axial line of the central axial line $S_2$' of the connected work member 10. The photographing camera 12 as the photographing instrument is disposed to decide the transverse direction to the rotating axial line as the photographing direction. An illuminating apparatus 14 as an illuminating instrument is arranged under a condition of opposing the photographing camera 12 interposing the connected work member 10, and an irradiating light is issued by a light source 14a from a rear side of the connected work member 10 toward the photographing camera 12.

Subsequently, the connected work member 10 is photographed by the photographing camera 12, and a photographed image is obtained (S110), and $F_2$, $G_2$, $G_2$' are determined as the reference points (S120) in positions corresponding to the reference points $F_1$, $G_1$, $G_1$' determined by the reference work member 100 on the outside outline $L_2$ (the outline $L_2$ of the work to be detected) of the connected work member 10 in the photographed image. As to determination of the reference point $F_2$ per member in the first metallic material 10a, the same technique as determining the reference point $F_2$ per member in the first metallic material 10a is practiced in the photographic image so as to determine the temporary image central axial line $S_2$ and the image central axial line $S_{20}$ for demanding the crossing point of the image central axial line $S_{20}$ and the outline $L_2$ of the work to be detected, thereby enabling to determine the reference point $F_2$ per member in the first metallic material 10a (the technique may be carried out as FIG. 13, and FIG. 6 shows an example that the temporary image central axial line $S_2$ agrees with the image central axial line $S_{20}$). Also as to the reference points $G_2$, $G_2$' per members in the second metallic material 10b, the technique like FIGS. 12A-12D may be applied similarly to the setting technique of the second reference work members $G_1$, $G_1$' in the second reference member 10b.

In the photographic image, the reference points are decided as FIG. 6, and based on these reference points, the ordering points of the detecting line (S130). The ordering points of the respective detecting lines are positioned by using the relative coordinate data stored as data 125a of the ordering point of the detecting line. Based on the positioned ordering points A to E and A' to E' of the detecting lines, the detecting line 102' is set between points E and E' (S140). It is confirmed whether the outline $L_2$ of the work to be detected exists or not on the set detecting line 102', and in case of not existing, it is judged that the protrudent adhered matters do not exist on the outside of the connected work member 10 as an object to be detected. Reversely, in case of existing on the detecting line 102', it is judged that the protrudent adhered matters exist on the outside of the connected work member 10 as an object to be detected (S150). When the image treatment (S150) is finished, the process advances to S160, and it is judged whether angle ranges to be inspected are all accomplished or not, and in case of not accomplishing, the process advances to S170, and the connected work member 10 is rotated at a prescribed angle, and obtaining a new photographic image, the treatments from S110 to S150 are repeated.

FIGS. 8A-8E shows a plurality of rotation displacing conditions of the connected work member 10 and the photographic images corresponding to the rotation displacing conditions. In FIGS. 8A-8E, all angle ranges to be photographed are 180°, and the connected work member 10 is rotated per 45° around the central axial line $S_2$' (FIG. 7), and in each of the angle positions, the photographic image is provided. FIGS. 8A to 8E show the examples of the images provided at the respective angle positions, and these images are performed with the image treatment in the same technique as FIG. 6 for detecting the protrudent adhered matters. The rotating angle intervals may be arbitrarily decided in response to diameter sizes of the objective connected work members, allowable heights (later mentioned allowable heights $H_1$) of the protrudent adhered matters, or detecting precision, and if the angle interval is too large, possibility of missing detection of the protrudent adhered matters S increases, but the treatment can be carried out at high speed. If making the interval small, the measuring frequency is increased, but the detection is done at high precision with less missing detection.

Prior to the above mentioned detecting treatment, the height (the allowable height $H_1$) allowing the protrudent adhered matters S from the outline $L_1$ of the reference work to exist is in advance decided. In case L is the distance between the outline $L_1$ of the reference work and the detecting line 102, the relation between the allowable height $H_1$ and the distance L may be decided to satisfy $0.3 \leq L/H_1 \leq 0.9$. If $L/H_1$ is less than 0.3, an abnormal condition is possibly exceedingly detected. If being more than 0.9, the measuring frequency must be many to cause the treatment to be delayed.

In case $H_1$ is the allowable height as mentioned above, and R is the diameter to be detected in the connected work member, the rotating angle θ to be decided may be adjusted to satisfy the following formula $$\theta \leq 2\cos^{-1}(R-H_1/R)$$

herein, 0<θ<180°. [Formula 1]

Figure 9:
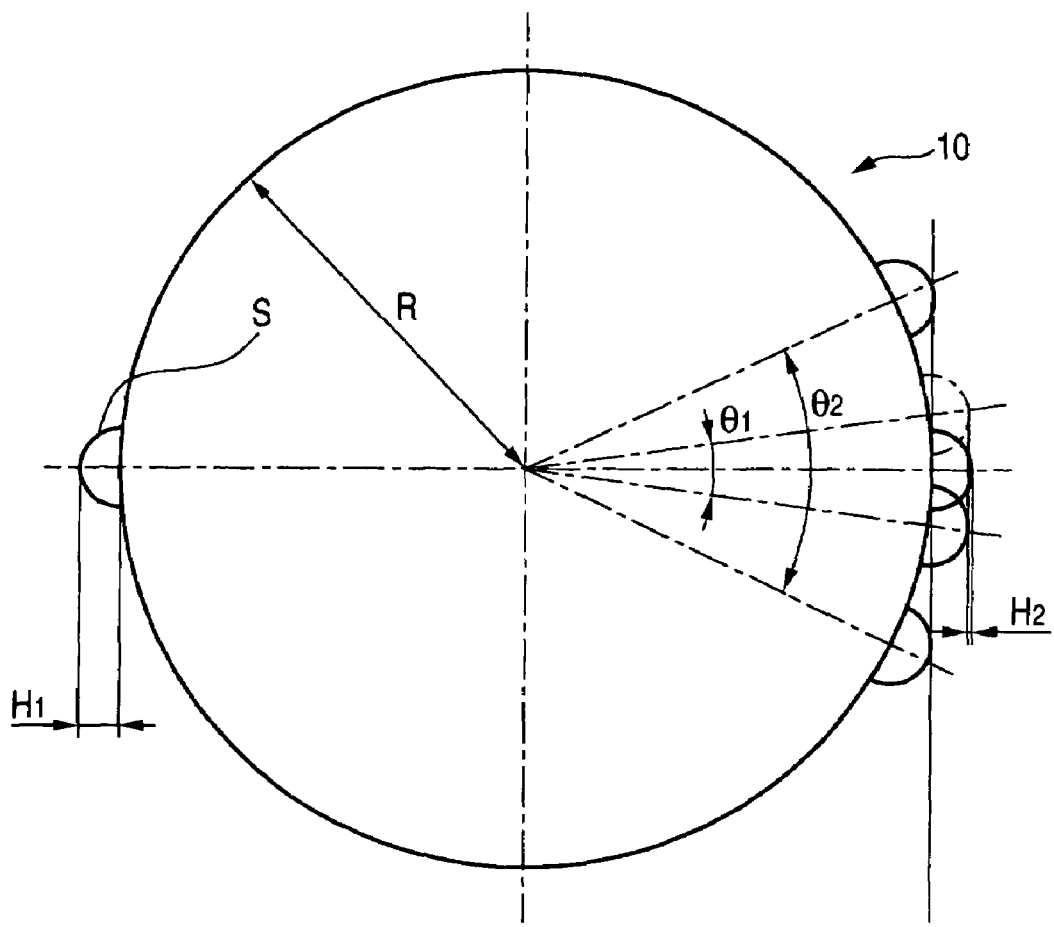
FIG. 9 is an explanatory view for explaining determination of rotation angles.

If increasing the rotating angle θ not to satisfy the above formula, the protrudent adhered matters do not possibly appear in the photographic image. In FIG. 9, θ2 is a boundary of the angle range having possibility that the protrudent adhered matters S do not appear in the photographic image.

Further, it is desirable to adjust the rotating angle θ to satisfy the following formula.

$d \leq 0.1$ herein, $d = R(1-\cos\theta)/H_1 = H_2/H_1$ $0 < \theta < 180°$. [Formula 2]

In the formula 2, θ is determined such that the difference $H_2$ is within 10% between the height of the protrudent matters S to be detected in the photographic image and the height of the actual protrudent adhered matters S. If $H_2/H_1 = 0.1$ in FIG. 9, the rotation angle θ is $\theta \leq \theta_1$. If an adjustment is as follows, the measurement is performed at high precision, while the measuring frequency can be reduced.

The above mentioned method of detecting the protrudent adhered matters may be applied to a method of detecting the protrudent adhered matters in spark plugs, and applied as one process in a method of making the spark plugs. Specifically, in a process of welding (for example, a laser welding) noble metal chips and a base metal in a central electrode of the spark plug, there may be provided a protrudent adhered matter detecting process of detecting presence or absence of the protrudent adhered matters on the central electrode surface, using the above method of detecting the protrudent adhered matters. In the following description, explanation will be made to the spark plug and the welding process therefore, referring to examples.

Figure 14:
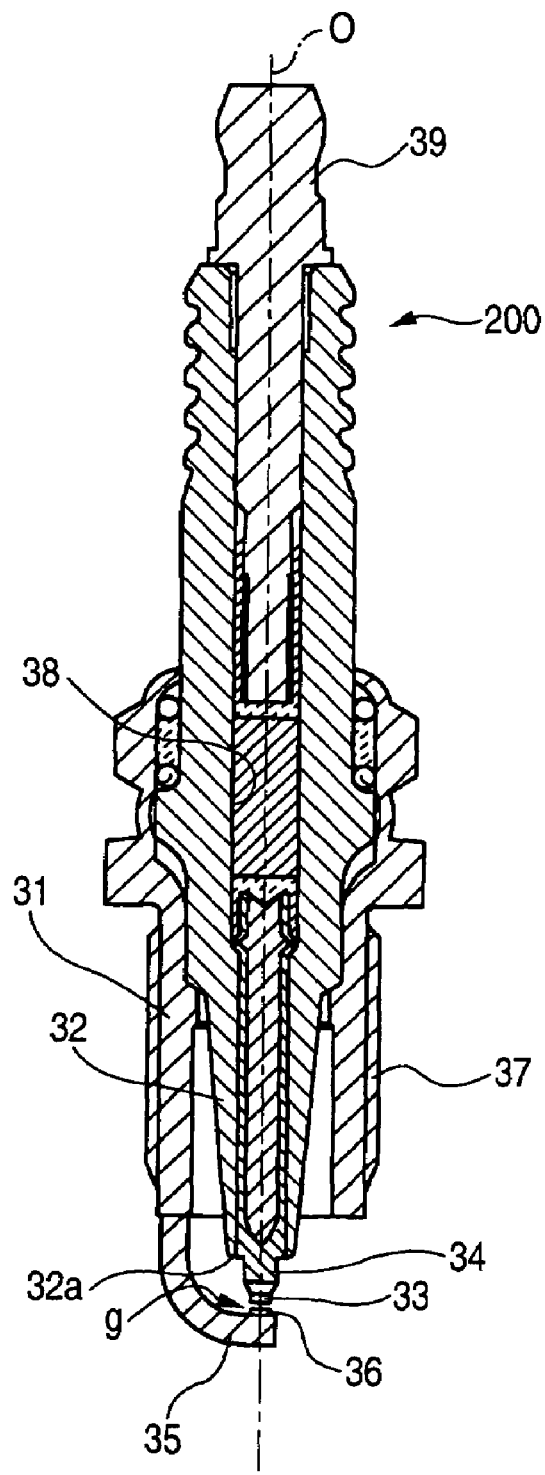
FIG. 14 is a vertically cross sectional view showing one example of a spark plug as an object to be detected as to the protrudent adhered matters and an enlarged view thereof.

The spark plug 200 shown in FIG. 14 comprises a cylindrical main metal body 31, an insulating body 32, a central electrode 34, and a ground electrode 35, said insulating body 32 being fitted inside of the main metal body 31 such that a front end portion of the insulating body 32 projects, said central electrode 34 being furnished inside of the insulating body 32 under a condition of projecting a firing portion 33 of noble metal (also called briefly as "the firing portion" hereafter), and said ground electrode 35 being welded at one end to the metal main body 31 and bent sideways at the other end arranged to oppose the front end portion of the central electrode 34. The ground electrode 35 is formed with a firing portion 36 of the noble metal (also called briefly as "the firing portion" hereafter) opposing the firing portion 33, and a space between the firing portion 33 and the opposing firing portion 36 is a spark discharging gap g.

The base materials of the electrode including the central electrode 34 and a chip-covered face portion of the ground electrode 35 are composed of a heat resistant alloy of a main component being Ni or Fe.

On the other hand, the firing portion 33 and the opposing firing portion 36 are composed of a precious metal of a main component being any one of Ir, Pt and Rh. With these precious metals, even under a condition where a temperature of the central electrode is ready for heightening, consumption resistance in the firing portions may be made good. A weldability for the central electrode 34 and the ground electrode 35 having the base material of the heat resistant alloy is also excellent. When using the precious metal having a base of such as Pt, favorably available other than Pt simplex are Pt—Ni alloy (for example, Pt—1 to 30 mass % Ni alloy), Pt—Ir alloy (for example, Pt—1 to 20 mass % Ir alloy), or Pt—Ir—Ni alloy. Being Ir of a main component, available are Ir—Ru alloy (for example, Ir—1 to 30 mass % Ru alloy), Ir—Pt alloy (for example Ir—1 to 10 mass % Pt alloy), Ir—Rh alloy (for example Ir—5 to 25 mass % Rh alloy, or Ir—Rh—Ni alloy (for example, Ir—1 to 40 mass % Rh—0.5 to 8 mass % Ni alloy).

Figure 15A:
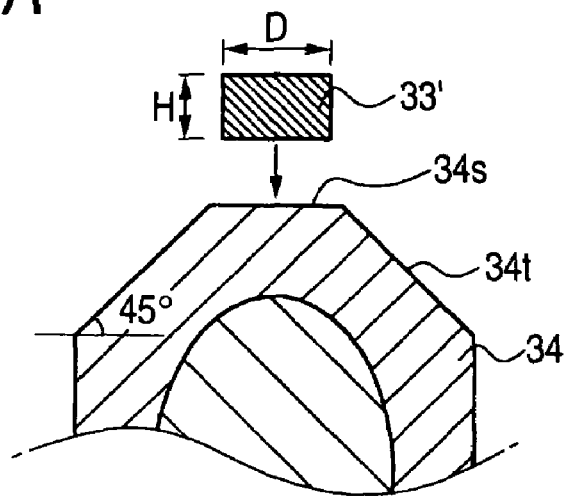
FIGS. 15A, 15B are explanatory views showing one example of a welding process of the spark plug of FIG. 14.
Figure 15B:
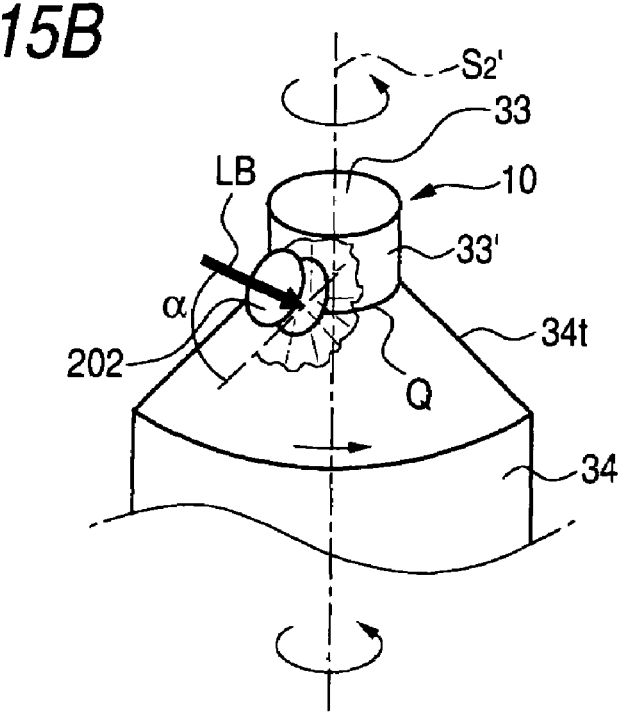

The central electrode 34 is, as shown in FIG. 15A, reduced in diameter of the front end side owing to a truncated conical taper 34t, and is laid on its front end face 34s with a chip 33' of the noble metal shaped in disk composed of an alloy composition composing the firing portion 33. Further, as shown in FIG. 15B, a laser beam LB is irradiated on a connected outer periphery thereof, so that a laser welded part 202 is formed on allover circumference (also called briefly as "the welded part" hereafter), and the firing portion 33 is formed by fixing the noble metal chip 33' (thereby, the above mentioned connected work member 10 is formed). The opposite firing portion 36 is provided by positioning the noble metal chip on the ground electrode 35 at the position corresponding to the firing portion 33 and forming the welded part on the outer periphery thereof. In case the firing portion 33 at the side of the central electrode 34 is composed of Ir based metal and the firing portion 36 at the side of the ground electrode 35 is composed of Pt based metal, it is possible to form the latter by a resistance welding connection. The noble metal chip used as mentioned above has, e.g., diameter D of 0.4 to 1.2 mm and thickness H of 0.5 to 1.5 mm.

After the welding process, the detecting process using the above mentioned detecting method of the protrudent adhered matters is performed, and in case the protrudent adhered matters appear on the surface of the central electrode after the welding connection and a process of removing the matters is carried out as a post-treating process with the detected results, a result will contribute to production of spark plugs of high quality. At this time, the base material of the electrode is the second metallic material 10a in FIG. 6, while the noble metal chip (the firing portion of the noble metal) is the first metallic material 10a in the same. The post-treating process is not limited to the removing process but to various kinds of, for example, post-treating processes such as are inspection process of carrying out a further inspection on members confirmed with occurrence of the protrudent adhered matters, otherwise a re-processing process of carrying out the re-process for satisfying a specification of a desired product, or a post-process which is assumed by those concerned in the field.

Besides, the post-process may use a product data-making process of making product data based on the inspected results. For example, if obtaining an information that a product is bad on the basis of the inspected result of the protrudent adhered matters, the product data making process may adopt methods of storing in a data base the information of the bad products (information concerning presence or absence of bad products, or concerning kinds of badness) in relation with a base information of the product (data of product number, inspection data, lot number). Thereby, having distinguished normal products and poor products at high precision, statistic managements are available.

INDUSTRIAL APPLICABILITY

In the instant example, the reference point is set to the connected work member using the method shown in FIG. 6, but in the connected work member of the photographic image obtained in the photographing process, when setting the reference point, the reference point cannot be set (for example, with the method as FIG. 6, the reference point cannot be set) and if the reference point cannot be set even after a fixed time passes, it is possible to regard as if the protrudent adhered matters (such as spatters) are adhered to positions to be the reference point. That is, based on a time taken for setting the reference point, it is possible to use a process of judging whether the connected work member occur at the position including the reference point or in the vicinity of the reference point. By using such a process, for example, if the reference point is not set in S120 of FIG. 5, since it is possible to judge the presence of the occurrence of the protrudent adhered matters at such a time, the protrudent adhered matters can be instantly detected though not setting the detecting line.

The invention has been explained through the practical example, but the invention is not limited thereto, and so far as not deviating out of the inventive scope, not limiting to the description of the inventive scope, getting over the scope easily substituted by those skilled in this technical field, it is possible to appropriately add improvements based knowledge ordinarily owned by those skilled.

What is claimed is:

1. A method of detecting protrudent matters adhered on an outside of a connected work member of a plurality of metallic materials wherein the connected work member is formed by connecting the plurality of metallic materials and the protrudent matters are caused by the connection of the plurality of metallic materials, the method, comprising:

a photographing process for photographing the connected work member by a photographing instrument to generate a photographic image;

a confirmation process of making an outside outline of the connected work member (also called as "outline of the work to be detected" hereafter) in the photographic image correspond to a range including a non-allowable range not allowing existence of the protrudent adhered matters and confirming presence or absence of the existence of the outline of the work to be detected in the non-allowable range;

a judging process of judging that the protrudent adhered matters exist on the outside of the connected work member when the existence of the outline of the work to be detected in the non-allowable range is confirmed in the confirmation process;

each of the plurality of the metallic materials includes a circular column portion, and the connected work member is formed by arranging and connecting the plurality of metallic materials coaxially;

making, in said confirmation process, correspondence between the outline of the work to be detected and a range including the non-allowable range in said photographic image, and confirming, in the corresponding photographic image, presence or absence of the existence of the outline of the work to be detected in the non-allowable range;

in advance deciding the non-allowable range on the basis of the outside outline (also called as "outline of the reference work" hereinafter) of a reference work material to be a reference of the connected work member;

previously setting, in the confirmation process, a detecting line as a boundary between the non-allowable range and an allowable range for allowing the existence of the outline of the reference work neighboring the non-allowable range on the basis of the outline of the reference work, making the correspondence between the detecting line and the outline of the work to be detected in the photographic image, and confirming whether or not the outline of the work to be detected exists on the detecting line; and in the confirmation process, making correspondence between the outline of the work to be detected and the detecting line in the photographic image, and confirming, in the photographic image, whether or not the outline of the work to be detected exists on the detecting line;

wherein the connected work member is formed to be axial, and when projecting toward an imaginary plan in parallel to a central axial line of the connected work member, the outline of the work to be detected in an orthogonal image is linearly symmetrical with respect to the central axial line (also called as "image central axial line" hereinafter) of the connected work member on the orthogonal image;

wherein in case one side concerning the image central axial line of the outline of the work to be detected of the linear symmetry is a first side and the other side is a second side, mutually symmetrical reference points are respectively set in the first side and the second side, and an ordering point (also called as "the ordering point of the first side detecting line" hereinafter) is determined for ordering a position of the first side on the basis of a reference point (also called as "the first side reference point" hereinafter) of the first side, and the positional relation between the first side reference point and the ordering point of the first side detecting line, as well as the positional relation between the second reference point and the ordering point (also called as "the ordering point of the second side detecting line" hereinafter) for prescribing the detecting line in the second side based on the second side reference point, are automatically settled to be symmetrical with respect to the central axial line on the basis of the first side reference point, the second side reference point and the ordering point of the first side detecting line;

wherein the photographing process rotates the connected work member per each of fixed angles around the rotation axial line of the central axial line, creates the photographic image of the connected work members in the respective angles, and performs the confirmation process in the respectively created photographic images.

2. The method of detecting the protrudent adhered matters as set forth in claim 1, comprising:

setting a reference point to be a positioning reference of the detecting line corresponding to the outline of the work to be detected in a prescribed position on the outline of the work to be detected, and positioning the detecting line to the outline of the work to be detected on the basis of the reference point.

3. The method of detecting the protrudent adhered matters as set forth in claim 1, comprising:

determining reference points per members in the plurality of metallic materials connected as elements of the connected work members, and positioning the detecting line per each of the metallic materials on the basis of the reference points per members.

4. The method of detecting the protrudent adhered matters as set forth in claim 3, wherein said plurality of metallic materials include two metallic members of different diameters, and in regard to at least one of these two metallic materials, a position of changing the diameter in the outline of the work to be detected is determined as a reference point per member.

5. The method of detecting the protrudent adhered matters as set forth in claim 1, wherein, in the outline of the reference work, a height $H_1$ (also called as "the allowable height $H_1$" hereafter) allowing the protrudent adhered matters to exist is in advance decided, and in case L is the distance between the outline of the reference work and the detecting line, the relation between the allowable height $H_1$ and the distance L is decided to satisfy $0.3 \leq L/H_1 < 0.9$.

6. The method of detecting the protrudent adhered matters as set forth in claim 1, wherein the connected work member is made by connecting the plurality of metallic materials by a laser weld or a resistance weld.

7. A method of making spark plugs, comprising a process of detecting the protrudent adhered matters by use of the method of detecting the protrudent adhered matters as set forth in claim 1, and a post-treating process for carrying out the post-treatment on the basis of detected results obtained by the detecting process of the protrudent adhered matters.

* * * * *